United States Patent [19]

Black et al.

[11] 3,968,216

[45] July 6, 1976

[54] METHOD OF INHIBITING HISTAMINE ACTIVITY WITH GUANIDINE COMPOUNDS

[75] Inventors: James Whyte Black, Hemel Hempstead; Graham John Durant, Welwyn Garden City; John Colin Emmett, Codicote; Charon Robin Ganellin, Welwyn Garden City, all of England

[73] Assignee: Smith Kline & French Laboratories Limited, Welwyn Garden City, England

[22] Filed: Nov. 25, 1974

[21] Appl. No.: 526,767

Related U.S. Application Data

[60] Division of Ser. No. 310,302, Nov. 29, 1972, Pat. No. 3,868,457, which is a continuation-in-part of Ser. No. 80,795, Oct. 14, 1970, abandoned.

[30] Foreign Application Priority Data

Oct. 29, 1969 United Kingdom.............. 52891/69

[52] U.S. Cl................................. 424/263; 424/269; 424/270; 424/273
[51] Int. Cl.²......................................... A61K 31/44
[58] Field of Search................. 424/263; 260/295 G

[56] References Cited

UNITED STATES PATENTS

| | | | |
|---|---|---|---|
| 2,928,829 | 3/1960 | Mull............................... | 260/295 G |
| 3,036,083 | 5/1962 | Mull............................... | 260/295 G |
| 3,278,542 | 10/1966 | Wollweber et al.............. | 260/295 G |
| 3,354,174 | 11/1967 | Bell................................ | 260/309.2 |

OTHER PUBLICATIONS

Derwent Pharmdoc. 586095–B Abstracting Belgian Patent No. 763744, published 3-9-71.

*Primary Examiner*—Norman A. Drezin
*Attorney, Agent, or Firm*—Joan S. Keps; Richard D. Foggio; William H. Edgerton

[57] ABSTRACT

A method of inhibiting histamine activity in particular inhibiting H-2 histamine receptors, by administering heterocyclicalkylguanidines.

5 Claims, No Drawings

METHOD OF INHIBITING HISTAMINE ACTIVITY WITH GUANIDINE COMPOUNDS

This is a division of Ser. No. 310,302 filed Nov. 29, 1972, now U.S. Pat. No. 3,868,457, which is a continuation-in-part of Ser. No. 80,795, filed Oct. 14, 1970, now abandoned.

This invention relates to a method of inhibiting histamine activity, and more particularly to inhibiting H-2 histamine receptors, with guanidine compounds. The compounds used in the methods of the invention normally exist as the addition salts, but for convenience, reference will be made throughout this specification to the parent compounds.

It has for long been postulated that many of the physiologically active substances within the animal body, in the course of their activity, combine with certain specific sites known as receptors. Histamine is a compound which is believed to act in such a way but, since the actions of histamine fall into more than one type, it is believed that there is more than one type of histamine receptor. The type of action of histamine which is blocked by drugs commonly called "antihistamines" (of which mepyramine is a typical example) is believed to involve a receptor which has been designated by Ash and Schild (*Brit. J. Pharmac. Chemother.* 27:427, 1966) as H-1. The substances and pharmaceutical compositions of the present invention are distinguished by the fact that they act at histamine receptors other than the H-1 receptor, that is they act at H-2 histamine receptors which are described by Black et al., Nature 236, 385 (1972). Black et al., cited above, page 390, column 2, state the following: "Mepyramine has been defined as an H₁-receptor antagonist [1] and burimamide has now been defined as an H₂-receptor antagonist. Used alone, burimamide can antagonize those responses to histamine, such as stimulation of acid gastric secretion, which cannot be blocked by mepyramine; histamine apparently activates H₂-receptors to produce these effects." Thus from the Black et al., paper, H-2 histamine receptors are those histamine receptors which are not inhibited by mepyramine but are inhibited by burimamide. Thus they are of utility in inhibiting certain actions of histamine which are not inhibited by the above-mentioned "antihistamines." Inhibitors of H-2 histamine receptors are useful, for example, as inhibitors of gastric acid secretion and as anti-inflammatory agents particularly where the inflammation is kinin-mediated.

The method of inhibiting H-2 histamine receptors according to this invention comprises administering internally to animals in an amount sufficient to produce such activity a guanidine of the following Formula 1 in which it is understood that the structure of the nucleus is such that the bond between the carbon and nitrogen atoms might equally well be represented as a double bond:

FORMULA I

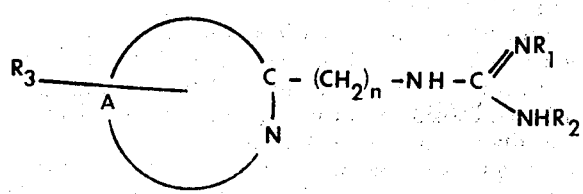

in which:
$n$ is 2 to 5;
A is a chain of 3 to 4 atoms of which 1 to 2 atoms are nitrogen or 1 of which is sulfur in the position alpha to the carbon atom and the remainder are carbon, which chain forms an unsaturated ring with the carbon and nitrogen atoms to which it is attached:

$R_1$ is hydrogen, alkyl having 1 to 4 carbon atoms, or benzyl;

$R_2$ is hydrogen, alkyl having 1 to 4 carbon atoms, benzyl, imidazolylethyl or amino or $R_1$ and $R_2$ together form an ethylene bridge and $R_3$ is hydrogen, alkyl having 1 to 4 carbon atoms, alkylthio having 1 to 4 carbon atoms or amino and pharmaceutically acceptable acid addition salts thereof.

Preferably A is such that it forms with the carbon and nitrogen atoms to which it is attached an imidazol-4(5)-yl ring. It is also preferred that $n$ is from 3 to 5 and $R_1$ and $R_2$ are both hydrogen or both methyl.

Processes for the preparation of the guanidines of Formula I commence with amines of the following Formula II:

FORMULA II

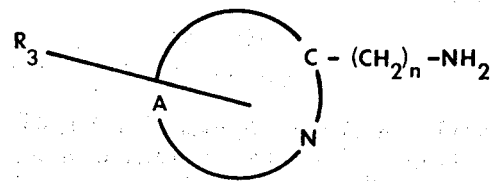

in which $n$, A and $R_3$ have the same significance as in Formula I.

The methods of synthesis of a number of these amines are described in detail in examples 9, 10, 11, 13, 18, 20, 21 and 24 hereinafter.

The amines of Formula II may be converted to the guanidines of Formula I by a number of routes but a particularly useful route is that which involves reaction in a suitable solvent such as water and/or an alcohol, or in certain circumstances in the absence of a solvent, with the acid addition salt of an S-alkyl-isothiourea preferably an S-methylisothiourea of the following general Formula III:

FORMULA III

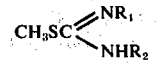

wherein $R_1$ and $R_2$ have the same significance as in Formula I. A complementary method of synthesis which may be carried out under similar conditions involves the reaction of an isothiourea of the following formula:

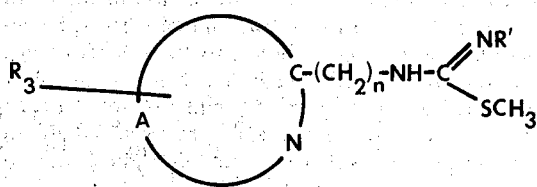

in which $n$, A and $R_3$ have the same significance as in Formula I and R' is hydrogen or methyl, with an appropriate amine.

The amines of Formula II may also be converted to the guanidines of Formula I by the following methods:
1. Reaction with an acid addition salt of a derivative of 3,5-dimethyl-1-guanyl-pyrazole of the Formula IV:

FORMULA IV

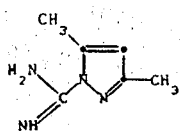

2. Reaction under similar conditions to those required for the process which utilizes the methylisothiourea of Formula III with the corresponding isourea of the Formula V:

Formula V

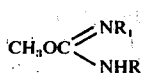

wherein $R_1$ and $R_2$ have the same significance as in Formula III.

3. Reaction with a cyanamide derivative having the Formula VI:

FORMULA VI

wherein $R_2$ has the same significance as in Formula I.

In Examples 14 and 15 hereinafter there are described alternative methods for the production of specific guanidines within the scope of our invention.

The compounds of Formula I may be combined with a pharmaceutically acceptable carrier to form pharmaceutical compositions. Advantageously the compositions will be made up in a dosage unit form appropriate to the desired mode of administration. The pharmaceutical carrier employed may be, for example, either a solid or liquid. Exemplary of solid carriers are lactose, terra alba, sucrose, talc, gelatin, agar pectin, acacia, magnesium stearate, stearic acid and the like. Exemplary of liquid carriers are syrup, peanut oil, olive oil, water and the like. Other pharmacologically active compounds may in certain cases be included in the pharmaceutical compositions.

As stated above, guanidine compounds of Formula I have been found to have pharmacological activity in the animal body as antagonists to certain actions of histamine which are not blocked by antihistamines such as mepyramine. For example, they have been found to inhibit selectively the histamine-stimulated secretion of gastric acid from the lumen-perfused stomachs of rats anaesthetised with urethane, at doses from 8 to 256 micromoles per kilogram intravenously. This procedure is described in the above-mentioned paper of Ash and Schild. Similarly, the action of these compounds and compositions may, in many cases, be demonstrated by their antagonism to the effects of histamine on other tissues which, according to the above-mentioned paper of Ash and Schild, are not H-1 receptors. Examples of such tissues are perfused isolated guinea-pig heart, isolated guinea-pig right atrium and isolated rat uterus.

The compounds of the method of this invention inhibit the secretion of gastric acid stimulated by pentagastrin or by food. In addition, these compounds also show anti-inflammatory activity in conventional tests such as the rat paw oedema test and u.v. erythema test. In the rat paw oedema test where the oedema is induced by bradykinin or by the histamine releasing agent known as compound 48/80, the paw volume is reduced significantly by subcutaneous injection of doses of about 500 micromoles/kg, i.e., a dose per single rat of about 15 mg. For example, in such a test, 3-(4(5)-imidazolyl) propyl guanidine reduced the volume of an oedema induced by 48/80 by 18%. The level of activity found for the compounds used in the method of the present invention is illustrated by the effective dose range in the anaesthetized rat, that is from 8 to 256 micromoles per kilogram, given intravenously, and also by the dose effective in the rat paw oedema test.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 1 gm. If a liquid carrier is used, the preparation may be in the form of a syrup, emulsion, soft gelatin capsule, sterile injectable liquid such as an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount to inhibit histamine activity. The route of administering may be orally or parenterally.

Preferably, each dosage unit will contain the active ingredient in an amount of from about 100 mg to about 250 mg.

The active ingredient will preferably be administered in equal doses three to six times per day. The daily dosage regimen will preferably be from about 750 mg to about 1000 mg.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition sales include those with hydrochloric, hydrobromic, hydriodic, sulphuric, picric and maleic acids.

Advantageously the composition will be made up in a dosage form appropriate to the desired mode of administration, for example as a tablet, capsule, injectable solution or, when used as an anti-inflammatory agent, as a cream for topical administration.

The invention is illustrated but in no way limited by the following examples.

EXAMPLE 1

Preparation of 3-(4(5)-imidazolyl)propylguanidine sulphate

Pure 4(5)-(3-amidazolyl)imidazole (10.5 g) is added to a solution of S-methylthiouronium sulphate (11.8 g) in water (125 ml). The resultant solution is refluxed for 4 hours, cooled and then acidified with the minimum quantity of sulphuric acid. Following concentration to low volume, ethanol is added which results in the separation of a colourless solid. This is filtered off, and twice recrystallized from water-methanol giving pure 3-(4(5)-imidazolyl)propylguanidine sulphate, m.p. 288°–290°C.

EXAMPLE 2

Preparation of 2-(4(5)-imidazolyl)ethylguanidine sulphate

A solution of histamine (55.5 g) and S-methylthiouronium sulphate (70.0 g) in water (300 ml) is heated under reflux for 6 hours. The crude material, isolated in a manner similar to that described in Example 1, is recrystallized from a minimum volume of water yielding pure 2-(4(5)-imidazolyl)ethylguanidine sulphate, m.p. 278°–279°C.

EXAMPLE 3

Preparation of 4-(4(5)-imidazolyl)butylguanidine sulphate

A solution of 4(5)-(4-aminobutyl)imidazole (1.61 g) and S-methylthiouronium sulphate (1.61 g) in water (20 ml) is heated under reflux for 3 hours. The product, isolated in a manner similar to that described in Example 1, is recrystallized from aqueous ethanol yielding 4-(4(5)-imidazolyl)butylguanidine sulphate, m.p. 311°–313°C (dec).

EXAMPLE 4

Preparation of N,N'-dimethyl-N''-[3-(4(5)-imidazolyl)propyl]-guanidine dihydrochloride A solution of 4(5)-(3-aminopropyl)imidazole (2.5 g) and N,N',S-trimethylisothiourea hydriodide (4.84 g) in water (30 ml) is heated under reflux for 48 hours. Concentration and recrystallization from isopropyl alcohol-hexane affords the product hydriodide, m.p. 168°–170°C. This is dissolved in water and treated with ethanolic picric acid yielding the dipicrate, m.p. 176°–179°C. This is treated with hydrochloric acid yielding the product dihydrochloride, m.p. 227°–229°C.

Methyl isothiocyanate (3.5 g) is added slowly to a solution of 4(5)-(3-aminopropyl)imidazole (6.0 g) in chloroform (50 ml). The resultant solution is heated under reflux for 1 hour and concentrated under reduced pressure to yield N-methyl-N'-[3-(4(5)-imidazolyl)propyl]thiourea as a semi-solid.

The crude thiourea (4.8 g) is converted into its hydriodide salt with 66% hydriodic acid (2.7 ml). This is dissolved in methanol (50 ml), methyl iodide (3.42 g) is added and the solution is heated under reflux for 2 hours. Concentration gives an oil which crystallizes in contact with nitromethane-ether. Further recrystallization from nitromethane-ether gives pure N,S-dimethyl-N'-[3-(4(5)-imidazolyl)propyl]isothiourea dihydriodide, m.p. 143°–145°C.

A solution of N,S-dimethyl-N'-[3-(4(5)-imidazolyl)propyl]-isothiourea dihydriodide (3.2 g) and 25% aqueous methylamine (6 ml) in water (20 ml) is heated in a pressure vessel at 100°C for 17 hours. After evaporation to dryness the residue is basified with aqueous potassium carbonate and evaporated to dryness. The dry residue is extracted with isopropyl alcohol, and the residue obtained from these extracts is converted into a picrate. Following recrystallization from ethanol the picrate (1.8 g, m.p. 174°–176°C) is converted into the hydrochloride (0.5 g) with hydrochloric acid. Recrystallization from ethanol of the combined samples from both syntheses yields pure N,N'-dimethyl-N''-[3-(4(5)-imidazolyl)propyl]guanidine dihydrochloride, m.p. 230°–231°C.

EXAMPLE 5

Preparation of N-methyl-N'-[3-(4(5)-imidazolyl)propyl]guanidine hydroiodide

A solution of 4(5)-(3-aminopropyl)imidazole (2.5 g) and N,S-dimethylisothiourea hydriodide (4.64 g) in ethanol (50 ml) is heated under reflux for 18 hours. Concentration followed by repeated recrystallization from isopropyl alcohol-ether affords N-methyl-N'-[3-(4(5)-imidazolyl)propyl]guanidine hydriodide, m.p. 169°–171°C.

EXAMPLE 6

Preparation of N-benzyl-N'-[3-(4(5)-imidazolyl)propyl]guanidine dihydrochloride A solution of 4(5)-(3-aminopropyl)imidazole (2.0 g) and N-benzyl-S-methylisothiourea hydriodide (4.9 g) in water (60 ml) is heated under reflux for 17 hours. Concentration followed by the addition of picric acid affords the guanidine dipicrate, m.p. 167°–169°C., from ethanol-water dimethylformamide. Treatment with hydrochloric acid followed by recrystallization from ethanol-ether affords N-benzyl-N'-[3-(4(5)-imidazolyl)propyl]guanidine dihydrochloride, m.p. 201.5°–203°C.

EXAMPLE 7

Preparation of N-(2-(4(5)-imidazolyl)ethyl)-N'-(3-(4(5)-imidazolyl)propyl)guanidine trimaleate Histamine is reacted with benzoyl isothiocyanate and the resulting N-benzoyl-N'-(2-(4(5)-imidazolyl)ethyl)-thiourea, after removing the benzoyl group, is converted to the hydriodide salt and then reacted with methyl iodide to give S-methyl-N-(2-(4(5)-imidazolyl)ethyl)-isothiourea dihydriodide.

Anhydrous potassium carbonate (0.97 g) is added gradually to a stirred aqueous solution of S-methyl-N-(2-(4(5)-imidazolyl)ethyl)isothiourea dihydriodide (5.5 g) and 4(5)-(3-aminopropyl)-imidazole (1.53 g). The resultant solution is heated under reflux for 5 hours. Additional potassium carbonate (1.5 g) is added and the solution is concentrated under reduced pressure. The dry residue is extracted with isopropyl alcohol and the concentrate of the extracts is treated with maleic acid (4.36 g) in isopropyl alcohol. Recrystallization from ethanol affords N-(2-(4(5)-imidazolyl)ethyl)-N'-(3-(4(5)-imidazolyl)propyl)guanidine trimaleate, m.p. 136°–138°C.

EXAMPLE 8

Preparation of N-amino-N'-(3-(4(5)-imidazolyl)propyl)guanidine hydriodide

A solution of 4(5)-(3-aminopropyl)imidazole (2.13 g) and S-methylisothiosemicarbazide hydriodide (3.97 g) in water (20 ml) is heated under reflux for 17 hours. Concentration followed by recrystallization from absolute alcohol gives N-amino-N'-(3-(4(5)-imidazolyl)propyl)guanidine hydriodide, m.p. 184°–187°C, is isolated from the filtrate.

EXAMPLE 9

Preparation of 3-(2-imidazolyl)propylguanidine sulphate

A mixture of 1-benzyl-2-(2-carbethoxyethyl)imidazole (10.32 g), methanol (15 ml) and redistilled ammonia (15 ml) is heated in an autoclave at 120°C for 24 hours. Concentration affords a green solid (9.35 g) which is dissolved in ethanol and chromatographed on an alumina column (pH 9, activity 1, Brockman scale). Elution with ethanol followed by concentration and recrystallization from ethyl acetate-petroleum ether (60°–80°C) affords 1-benzyl-2-(2-carboxamidoethyl)imidazole, m.p. 135°–136°C.

The amide (5.9 g) dissolved in tetrahydrofuran is reduced with diborane generated externally from 1M sodium borohydride in diglyme (300 ml) and boron trifluoride etherate (65 g). The clear solution obtained is heated under reflux for 17 hours, excess concentrated hyrochloric acid is added and the resulting solution heated under reflux for 2 hours. Following concentration, excess 10N sodium hydroxide is added and the solution is extracted with chloroform (6 × 50 ml). The combined organic extracts are dried over sodium sulphate, concentrated and the residue treated with picric acid (12.4 g) in nitromethane. Recrystallization from aqueous ethanol affords 1-benzyl-2-(3-aminopropyl)imidazole dipicrate, m.p. 165°–167°C.

The picrate is converted into the hydrochloride (2.85 g) with hydrochloric acid in the normal way and then dissolved in liquid ammonia, and treated directly with small pieces of sodium (total 1 g) until the persistence of a permanent blue colour. Ammonium chloride (1.65 g) is added and excess ammonia removed by evaporation. A solution of sodium carbonate (1.0 g) in water (12 ml) is added and the solution is concentrated under reduced pressure. The residue is extracted with hot ethanol and the concentrated extracts are treated with aqueous picric acid (4.6 g). Cooling affords 2-(3-aminopropyl)imidazole dipicrate, m.p. 207°–209°C.

Treatment of the picrate with hydrochloric acid in the normal way, followed by recrystallization of the product from isopropyl alcohol-ethanol-ether affords 2-(3-aminopropyl)imidazole dihydrochloride as a hygroscopic solid, m.p. 148°–150°C.

A solution of 2-(3-aminopropyl)imidazole, prepared from its dihydrochloride (0.9 g) by means of an ion-exchange resin (OH⁻), and S-methylthiouronium sulphate (1.26 g) in water (20 ml) is heated under reflux for 18 hours. The product, isolated in a manner similar to that described in Example 1, is recrystallized from aqueous ethanol yielding 3-(2-imidazolyl)propylguanidine sulphate monohydrate, m.p. 260°–262°C (dec.).

EXAMPLE 10

Preparation of 4-(2-imidazolyl)butylguanidine dihydrochloride

A solution of 1-benzyl-2-(2-carbethoxyethyl)imidazole (5.2 g) in dry ether (150 ml) is added, dropwise, to a stirred suspension of aluminum lithium hydride (1.0 g) in dry ether (150 ml) at gentle reflux. The suspension is subsequently heated under reflux for 2 hours, and then cooled during the successive addition of water (1 ml), 15% sodium hydroxide (1 ml) and water (3 ml). After heating under reflux for 0.5 hour and filtration, the insoluble solid is extracted with hot methanol (3 × 100 ml). The combined organic extracts are concentrated under reduced pressure and the residue dissolved in 2N hydrochloric acid. Following extraction with chloroform, the solution is basified with solid potassium carbonate. Chloroform extracts of the basic solution are dried over sodium sulphate and concentrated under reduced pressure, affording 1-benzyl-2-(3-hydroxypropyl) imidazole as a colorless viscous liquid (4.6 g). The carbinol (4.4 g) is dissolved in benzene (40 ml) and added to thionyl chloride (20 ml) at reflux temperature. After complete addition, water (four drops) is added and the mixture is heated under reflux for 0.5 hour. Concentration followed by the addition of cyclohexane yields a yellow solid. Recrystallization from ethanol-ether yields 1-benzyl-2-(3-chloropropyl)imidazole hydrochloride, m.p. 162°–164°C.

1-Benzyl-2-(3-chloropropyl)imidazole hydrochloride (2.7 g) is added to a stirred suspension of anhydrous sodium cyanide (2.43 g) in dry dimethyl sulphoxide at 30°–45°C. After 3 hours, the reaction mixture is diluted with dichloromethane (75 ml) and then extracted with water (4 × 50 ml). The organic extracts are dried over magnesium sulphate, concentrated and the residue dissolved in ethanol and treated with an aqueous solution of picric acid. The picrate obtained is recrystallized from water, affording 1-benzyl-2-(3-cyanopropyl) imidazole picrate, m.p. 100°–102°C.

Treatment of the picrate (1.14 g) with hydrochloric acid in the usual way followed by recrystallization from ethanol-ether affords 1-benzyl-2-(3-cyanopropyl)imidazole hydrochloride, m.p. 159°–161°C.

1-Benzyl-2-(3-cyanopropyl)imidazole, prepared from the hydrochloride (2.6 g) by means of ion-exchange resin (OH⁻), is dissolved in methanol saturated with ammonia (65 ml). Raney nickel (1 g) is added and hydrogenation is performed at 130°C under 140 atmospheres of hydrogen for 4 hours. Following filtration and concentration the product is converted into the picrate. Recrystallization from isopropyl alcohol-water affords 1-benzyl-2-(4-aminobutyl)imidazole dipicrate, m.p. 167°–169°C.

1-Benzyl-2-(4-aminobutyl)imidazole dipicrate (15.0 g) is converted into its dihydrochloride and caused to react with sodium in liquid ammonia according to the method described in Example 9. The product is isolated as its picrate, which is recrystallized from aqueous ethanol affording 2-(4-aminobutyl)-imidazole dipicrate, m.p. 194°–195°C.

Treatment of the picrate (8.7 g) with hydrochloric acid in the normal way, followed by recrystallization from isopropyl alcohol-ethanol-ether yields 2-(4-aminobutyl)imidazole dihydrochloride as a hygroscopic solid, m.p. 229°–231°C.

A solution of 2-(4-aminobutyl)imidazole, prepared from its dihydrochloride (1.12 g) by means of ion-exchange resin (OH⁻), and S-methylthiouronium sulphate (0.78 g) in water is heated under reflux for 60 hours. The reaction product is isolated as its dipicrate, m.p. 227°–227°C (from aqueous nitromethane).

Treatment of the picrate with hydrochloric acid in the normal way, followed by recrystallization from isopropyl alcohol-ether affords 4-(2-imidazolyl)butylguanidine dihydrochloride, m.p. 189°–191°C.

EXAMPLE 11

Preparation of 3-(1-methyl-4-imidazolyl)propylguanidine dimaleate

A mixture of 4(5)-(3-aminopropyl)imidazole (16 g)

and acetic anhydride (30 ml) is heated under reflux for 1 hour. After cooling, water (60 ml) is added and the solution concentrated to dryness under reduced pressure. A further quantity of water (60 ml) is added to the residual oil and the mixture evaporated to dryness to give the N-acetyl derivative as an oil which is not purified further. Dimethyl sulphate (7.6 ml) is then added dropwise to a stirred solution of this crude oil in 10% aqueous sodium hydroxide (100 ml) during which time the temperature is maintained between 20°–30°C. After the addition, further quantities of sodium hydroxide (100 ml) and dimethyl sulphate (7.6 ml) are added as before and finally the solution is heated for 45 minutes on a steam bath. After cooling, the solution is saturated with sodium sulphate, extracted with chloroform (9 × 100 ml) and the chloroform extracts evaporated to dryness. The residue is dissolved in 6N hydrochloric acid (300 ml) and the solution heated under reflux overnight. Evaporation to dryness gives an oily residual hydrochloride, which is dissolved in water and converted into the picrate by the addition of an ethanolic solution of picrate acid. The crude picrate obtained is recrystallized three times from ethanol-water to give the isomerically pure dipicrate, m.p. 190°–191°C. An analytically pure sample has m.p. 194°–196°C. 1-Methyl-4-(3-aminopropyl)imidazole dihydrochloride (4.8 g, m.p. 254°–256°C) is obtained from the dipicrate in the usual way with hydrochloric acid. Recrystallization of the dihydrochloride from methanol/ether gives a pure sample m.p. 258°–259°C.

An aqueous solution of S-methylthiouronium sulphate (2.43 g) is added to a solution prepared from the amine dihydrochloride (3.7 g) and sodium hydroxide (1.4 g) in water. The resultant solution is heated under reflux for 17 hours. Concentration and acidification with dilute sulphuric acid yields the crude guanidine sulphate which is treated with an excess of ethanolic picric acid. The picrate obtained is recrystallized from methanol-dimethylformamide-water to yield the pure dipicrate, m.p. 206°–208°C. Treatment with hydrochloric acid in the normal way yields the hydrochloride which is converted into the free base with aqueous potassium carbonate followed by evaporation to dryness. The ethanol extracts of the base are treated with ethanolic maleic acid and ether yielding a maleate salt. Recrystallization from ethanol-ether gives 3-(1-methyl-4-imidazolyl) propylguanidine dimaleate, m.p. 146°–147.5°C.

EXAMPLE 12

Preparation of 2-(1-methyl-4-imidazolyl)ethylguanidine sulphate

An aqueous solution of S-methylthiouronium sulphate (2.1 g) is added to a solution prepared from 1-methyl-4-(2-aminoethyl)imidazole dihydrochloride (3.0 g) and sodium hydroxide (1.21 g) in water. The resultant solution is heated under reflux for 17 hours. The product, isolated in a manner similar to that described in Example 1 is recrystallized from aqueous ethanol yielding pure 2-(1-methyl-4-imidazolyl)ethylguanidine sulphate, m.p. 280°–282°C.

EXAMPLE 13

Preparation of 3-(2-methyl-4(5)-imidazolyl)propylguanidine dihydrochloride

A hot solution of 1-bromo-5-phthalimidopentan-2-one (31.0 g) in dry ethanol (500 ml) and dimethylformamide (100 ml) is added over 3 hours to a solution prepared from acetamidine hydrochloride (28.9 g) and sodium ethoxide (from sodium, 6.9 g) in dry ethanol (800 ml). After addition the mixture is heated under reflux for 2 hours and then allowed to cool. Following filtration and concentration under reduced pressure, the residue is dissolved in ethanol and acidified with a solution of hydrogen chloride in ethanol. The solution is filtered, concentrated and carefully diluted with ethyl acetate. The solid obtained is recrystallized from ethanol-ethyl acetate to give 2-methyl-4(5)-(3-phthalimidopropyl)imidazole hydrochloride, m.p. 216°–217°C. An analytically pure sample, m.p. 234°–236°C, is obtained by further recrystallization. The addition of aqueous potassium carbonate liberates the base, m.p. 157°–159°C. Hydrolysis of 2-methyl-4(5)-(3-phthalimidopropyl)imidazole (4.95 g) with 5N hydrochloric acid gives 2-methyl-4 (5)-(3-aminopropyl)imidazole dihydrochloride, m.p. 188°–192°C. An analytically pure sample obtained by recrystallization from ethanol-ether has m.p. 193°–195°C.

An aqueous solution of S-methylthiouronium sulphate (1.18 g) is added to a solution prepared from the amine dihydrochloride (1.8 g) and sodium hydroxide (0.68 g) in water. The resultant solution is heated under reflux for 17 hours, concentrated and the residue treated with an excess of ethanolic picric acid. The picrate obtained is recrystallized from ethanol-water-dimethylformamide to yield pure 3-(2-methyl-4(5)-imidazolyl)propylguanidine dipicrate, m.p. 213°–216°C. Treatment with hydrochloric acid in the normal way yields 3-(2-methyl-4(5)-imidazolyl)propylguanidine dihydrochloride, m.p. 190°–192°C.

EXAMPLE 14

Preparation of 3-(2-methylthio-4(5)-imidazolyl)propylguanidine dihydrochloride

A solution of 3-(2-thio-4(5)-imidazolyl)propylguanidine hydrochloride (0.35 g) in methanolic hydrogen chloride is heated under reflux for 3 hours. Concentration and cooling affords 3-(2-methylthio-4(5)-imidazolyl)propylguanidine dihydrochloride, m.p. 217°–219°C.

EXAMPLE 15

Preparation of 3-(2-amino-4(5)-imidazolyl)propylguanidine dihydrochloride

Freshly prepared 2–3% sodium amalgam (950 g, obtained from the addition of 23.8 g sodium to 1020 g mercury in the laboratory atmosphere) is added in ca. 25 g portions during 75 minutes to a stirred solution of L-arginine ethyl ester dihydrochloride (39.8 g) in water (250 ml) - ethanol (150 ml) at −12°C. After each portion of amalgam has been added, powdered carbon dioxide and 5N hydrochloric acid are added to maintain the temperature at −12° to −10°C and the pH at 2.5. Stirring is continued for a further 45 minutes with addition of acid, as necessary, to maintain the pH until the mixture has warmed to at least +10°C. The mixture is then decanted from the liberated mercury and filtered; cyanamide (19.3 g) is added and the mixture is warmed at 50°C for 30 minutes, then left at 0°C for 18 hours and concentrated to dryness. The residue is finally dried by addition to ethanol followed by reconcentration. It is washed with ether (3 × 100 ml) to remove any unchanged cyanamide and then extracted with absolute ethanol (500 ml) at 50°C. The extract is cooled, filtered, concentrated to 50 ml, stirred with decolourising charcoal, filtered and heated with hot ethanolic picric acid. The resulting picrate (76 g) is crystallized from ethanol. O-Ethyl isourea picrate (18.3 g, m.p. 189°–192°C) which crystallizes first is removed and the filtrate is concentrated to low volume and cooled. 3-(2-Amino-4(5)-imidazolyl)propylguanidine dipicrate, which crystallizes, is collected (52.5 g.), m.p. 247°–249°C. A sample, recrystallized from ethanol, has m.p. 249°–251°C. The above guanidine dipicrate (23 g.) is converted into its hydrochloride using hydrochloric acid. The crude product (8.5 g.) is recrystallized from ethanol. Following removal of a first crop of impure material (3.8 g.), the addition of ether affords pure 3-(2-amino-4(5)-imidazolyl)propylguanidine dihydrochloride, m.p. 193°–194°C.

EXAMPLE 16

Preparation of 3-[3-(1,2,4-triazolyl)]propylguanidine nitrate

A solution of 3-(3-aminopropyl)-1,2,4-triazole dihydrochloride (5.53 g) and potassium hydroxide (3.12 g) in anhydrous ethanol is heated under reflux for 30 minutes. Following filtration, 3,5-dimethyl-1-amidinopyrazole nitrate (5.56 g) is added and the solution is heated under reflux for 8 hours. Concentration and ether extraction affords a residual semi-solid, which is recrystallized from ethanol-ether yielding 3-[3-(1,2,4-triazolyl)]propylguanidine nitrate, m.p. 116°–118°C.

EXAMPLE 17

Preparation of 2-[3-(1,2,4-triazolyl)]ethylguanidine sulphate

A solution of 3-(2-aminoethyl)-1,2,4-triazole (prepared from 3-(2-aminoethyl)-1,2,4-triazole dihydrochloride (2.0 g) and sodium (0.51 g) in ethanol) and S-methylthiouronium sulphate (1.6 g) in water (50 ml) is heated under reflux for 2.5 hours. The crude product is recrystallized from aqueous isopropyl alcohol, yielding 2-[3-(1,2,4-triazolyl)]ethylguanidine sulphate monohydrate, m.p. 125°–127°C.

EXAMPLE 18

Preparation of 3-(2-pyridyl)propylguanidine sulphate 2-(2-Cyanoethyl)pyridine is reduced with lithium aluminum hydride in ether, in the normal way, yielding 2-(3-aminopropyl) pyridine, b.p. 77°C/0.4 mm. (Dihydrochloride, m.p. 175°–177°C).

A solution of 2-(3-aminopropyl)pyridine (2.72 g) and S-methylthiouronium sulphate (2.78 g) in water (40 ml) is heated under reflux for 28 hours. The product isolated by the manner described in Example 1 was recrystallized from methanol, yielding 3-(2-pyridyl)-propylguanidine sulphate, m.p. 185°–187°C.

EXAMPLE 19

Preparation of 2-(2-pyridyl)ethylguanidine sulphate

A solution of 2-(2-aminoethyl)pyridine (10.0 g) and S-methylthiouronium sulphate (11.39 g) in water (30 ml) is heated under reflux for 2 hours. The crude material, isolated in a manner similar to that described in Example 1, is recrystallized from water, yielding 2-(2-pyridyl)ethylguanidine sulphate, m.p. 264°–266°C.

EXAMPLE 20

Preparation of 3-(3-pyrazolyl)propylguanidine hemisulphate

Aluminum chloride (43 g) is added to a stirred solution of 4-phthalimidobutyryl chloride (36.2 g) in 1,1,2,2-tetrachloroethane (400 ml), previously saturated with acetylene. Acetylene is bubbled through the solution overnight, with stirring, and the reaction mixture is then decomposed by the addition of crushed ice (300 g). The organic layer is separated and the aqueous layer extracted with 1,1,2,2-tetrachloroethane (3 × 100 ml). The combined organic solution is dried over sodium sulphate and concentrated. The residual solid is recrystallized from hexane affording 1-chloro-6-phthalimidohex-1-en-3-one, m.p. 92°C.

This is immediately caused to react with hydrazine hydrate (19.2 g) at 95°C for 10 minutes. Following concentration, the residue is extracted with ether in a Soxhlet apparatus for three days. Concentration of the ether extract affords 3-(3-aminopropyl)pyrazole.

The dipicrate has m.p. 194°C (from nitromethane).

An intimate mixture of 3-(3-aminopropyl)pyrazole (4.7 g) and S-methylthiouronium sulphate (4.9 g) is fused at 140°C for one hour. After cooling, methanol is added and the filtered methanol solution is subsequently diluted with ethanol. The solid obtained is recrystallised from methanol-ethanol affording 3-(3-pyrazolyl) propylguanidine hemisulphate, m.p. 210°C.

EXAMPLE 21

Preparation of 3-(2-thiazolyl)propylguanidine hemisulphate

A mixture of 3-phthalimidothiobutyramide (15.0 g) and bromoacetaldehyde diethyl acetal (19.7 g) is heated at 100°C with frequent agitation for 2 hours. The solid mass is extracted with hot ethanol, and the extracts are treated with charcoal and filtered. On cooling, crystals are deposited. These are dissolved in water (50 ml) and the solution washed with ether (25 ml) and diluted with aqueous sodium acetate to pH 6. A yellowish-brown solid crystallizes out which is collected and washed with water yielding 3-(2-thiazolyl)propylphthalimide hydrobromide, m.p. 67°–70°C. The phthalimido derivative (5.0 g) is dissolved in ethanol (50 ml), hydrazine hydrate (2 ml) is added and the solution heated under reflux for 2 hours. The solvent is removed under reduced pressure and the residue is dissolved in concentrated hydrochloric acid (30 ml) and heated under reflux for 1 hour. After cooling, phthalhydrazide is removed by filtration and the filtrate evaporated to dryness. The residue is recrystallized from methanol-ether yielding 3-(2-thiazolyl) propylamine dihydrochloride, m.p. 160°–165°C.

3-(2-Thiazolyl)propylamine (2.7 g) (prepared from the amine dihydrochloride by reaction with aqueous sodium hydroxide and extraction with ethyl acetate) is mixed intimately with finely powdered S-methylthiouronium sulphate (5.3 g) and the mixture is heated at 140°–150°C for 1 hour. After cooling, the mass is extracted with hot ethanol several times, and the combined extracts are diluted with ether which causes the precipitation of a white solid. Recrystallization from aqueous ethanol yields 3-(2-thiazolyl)propylguanidine hemisulphate, m.p. 160°–163°C.

EXAMPLE 22

Preparation of
2-[3-(4(5)-imidazolyl)propyl]amino-2-imidazoline dihydrochloride

A mixture of 4(5)-(3-aminopropyl)imidazole (2.5 g), 2-methylthio-2-imidazolinium sulphate (4.3 g) and 1N potassium hydroxide (20 ml) is heated under reflux for 66 hours. The reaction product is converted into the picrate (1.7 g), m.p. 246°–250°C (from ethanoldimethylformamide). Treatment of picrate (1.2 g) with hydrochloric acid yields 2-(3-(4(5)-imidazolyl)propyl-)amino-2-imidazoline dihydrochloride, m.p. 130°–134°C.

EXAMPLE 23

Preparation of 2-(2-thiazolyl)ethylguanidine hemisulphate

An intimate mixture of 2-(2-aminoethyl)thiazole (4.5 g) and S-methylthiouronium sulphate (9.8 g) is heated at 140°–150°C for 1 hour. Extraction with ethanol and cooling affords the crude product, m.p. 130°–135°C. Recrystallization from ethanol gives 2-(2-thiazolyl)ethylguanidine hemisulphate, m.p. 143°–145°C.

EXAMPLE 24

Preparation of 5-(4(5)-imidazolyl)pentylguanidine sulphate i. A mixture of 1-bromo-7-phthalimidoheptan-2-one (60.0 g) (obtainable from epsilon-aminocaproic acid) and formamide (360 ml) was heated at 180°–185°C for 2 hours. Following removal of excess formamide by distillation under reduced pressure, the residue was hydrolyzed by heating (under reflux) with 5N hydrochloric acid (1.8 l) for 18 hours. After cooling to 0° and filtration to remove phthalic acid, the filtrate was concentrated under reduced pressure and the residue extracted with hot ethanol and again concentrated. The residual amine hydrochloride was converted to the free base by passage down Amberlite ion-exchange resin IRA 401 (OH$^-$) and elution with methanol. The base obtained was converted into the picrate with picric acid (82.5 g) in water. The picrate was recrystallized several times from water affording 4(5)-(5-aminopentyl-)imidazole dipicrate (55 g) m.p. 209°–211° (from nitromethane).

The picrate was treated with hydrochloric acid in the usual way yielding the amine dihydrochloride (24.6 g) which was finally converted to 4(5)-(5-aminopentyl-)imidazole (15.3 g), m.p. 45°–8° by passage down ion-exchange resin Amberlite IRA-401 (OH$^-$).

ii. A solution of 4(5)-(5-aminopentyl) imidazole (1.53 g) and S-methylthiouronium sulphate (1.39 g) in water (10 ml was heated under reflux for 3 hours. The product, isolated in a manner similar to that described in Example 1 was recrystallized from aqueous ethanol yielding 5-(4(5)-imidazolyl)pentylguanidine sulphate (2.0 g), m.p. 278°–280°.

EXAMPLE 25

| Ingredients | Amounts |
|---|---|
| 3-(4(5)-imidazolyl)propylguanidine sulphate | 150 mg |
| Sucrose | 75 mg |
| Starch | 25 mg |
| Talc | 5 mg |
| Stearic acid | 2 mg |

The ingredients are screened, mixed and filled into a hard gelatin capsule.

EXAMPLE 26

| Ingredients | Amounts |
|---|---|
| N,N'-dimethyl-N''-[3-(4(5)-imidazolyl)propyl]-quanidine dihydrochloride | 200 mg |
| Lactose | 100 mg |

The ingredients are screened, mixed and filled into a hard gelatin capsule.

The capsules prepared as in Examples 5 and 6 are administered orally to a subject having excessive gastric acid secretion within the dose ranges given hereabove.

What is claimed is:

1. A method of inhibiting H-2 histamine receptors, said H-2 histamine receptors being those histamine receptors which are not inhibited by mepyramine but are inhibited by burimamide, which comprises administering internally to an animal requiring inhibition of said H-2 histamine receptors in an amount sufficient to inhibit said H-2 histamine receptors a compound of the formula:

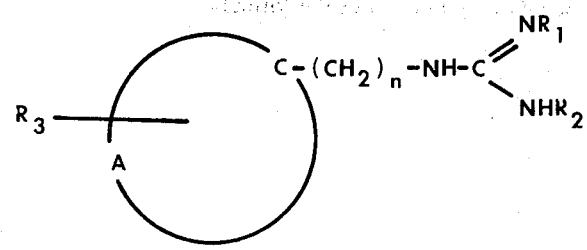

in which:
n is 2 to 5;
A taken together with the carbon and nitrogen atoms to which it is attached forms a pyridine ring;
$R_1$ is hydrogen, alkyl having 1 to 4 carbon atoms or benzyl;
$R_2$ is hydrogen, alkyl having 1 to 4 carbon atoms, benzyl, imidazolylethyl or amino or $R_1$ and $R_2$ together form an ethylene bridge and
$R_3$ is hydrogen, alkyl having 1 to 4 carbon atoms, alkylthio having 1 to 4 carbon atoms or amino or pharmaceutically acceptable acid addition salts thereof.

2. A method according to claim 1 in which the compound is 3-(2-pyridyl)propylguanidine.

3. A method according to claim 1 in which the compound is 2-(2-pyridyl)ethylguanidine.

4. A method of inhibiting gastric acid secretion which comprises administering internally to an animal requiring inhibition of gastric acid secretion in an amount sufficient to inhibit gastric acid secretion a compound of the formula

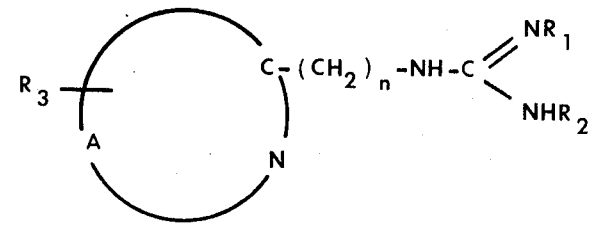

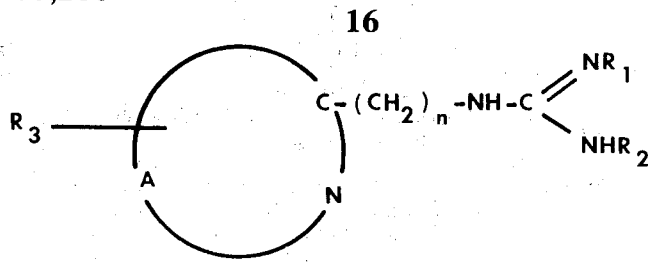

in which:
 n is 2 to 5
 A taken together with the carbon and nitrogen atoms to which it is attached forms a pyridine ring;
 $R_1$ is hydrogen, alkyl having 1 to 4 carbon atoms or benzyl;
 $R_2$ is hydrogen, alkyl having 1 to 4 carbon atoms, benzyl, imidazolylethyl or amino or $R_1$ and $R_2$ together form an ethylene bridge and
 $R_3$ is hydrogen, alkyl having 1 to 4 carbon atoms, alkylthio having 1 to 4 carbon atoms or amino or pharmaceutically acceptable acid addition salts thereof.

5. A method of producing anti-inflammatory activity which comprises administering to an animal requiring said activity in an amount sufficient to produce said activity a compound of the formula:

in which:
 n is 2 to 5;
 A taken together with the carbon and nitrogen atoms to which it is attached forms a pyridine ring;
 $R_1$ is hyrogen, alkyl having 1 to 4 carbon atoms or benzyl;
 $R_2$ is hydrogen, alkyl having 1 to 4 carbon atoms, benzyl, imidazolylethyl or amino or $R_1$ and $R_2$ together form an ethylene bridge and
 $R_3$ is hydrogen, alkyl having 1 to 4 carbon atoms, alkylthio having 1 to 4 carbon atoms or amino or pharmaceutically acceptable acid addition salts thereof.

* * * * *

UNITED STATES PATENT AND TRADEMARK OFFICE
CERTIFICATE OF CORRECTION

PATENT NO. : 3,968,216
DATED : July 6, 1976
INVENTOR(S) : James Whyte Black, Graham John Durant, John Colin Emmett and Charon Robin Ganellin It is certified that error appears in the above-identified patent and that said Letters Patent are hereby corrected as shown below:

Column 14, lines 27-37, the formula should appear as follows:

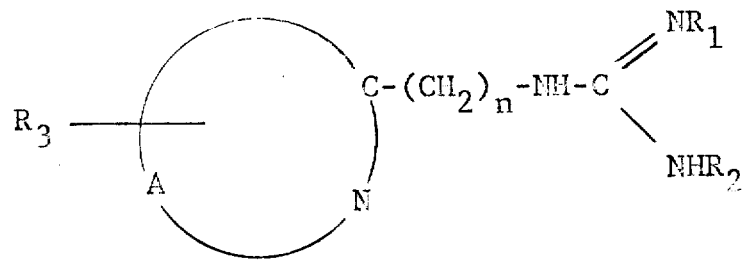

Signed and Sealed this

Second Day of November 1976

[SEAL]

Attest:

RUTH C. MASON
*Attesting Officer*

C. MARSHALL DANN
*Commissioner of Patents and Trademarks*